United States Patent [19]
Schultz et al.

[11] Patent Number: 6,117,651
[45] Date of Patent: Sep. 12, 2000

[54] EXPRESSION VECTORS

[75] Inventors: Jody Schultz, Seattle, Wash.; Gary Hermanson, Encinitas, Calif.

[73] Assignee: Neose Technologies, Inc., Horsham, Pa.

[21] Appl. No.: 08/965,850

[22] Filed: Nov. 7, 1997

Related U.S. Application Data

[60] Provisional application No. 60/029,545, Nov. 8, 1996.

[51] Int. Cl.[7] .................................................. C12N 15/00
[52] U.S. Cl. .................. 435/69.1; 435/71.1; 435/252.3; 435/252.33; 536/23.1; 536/23.2; 536/23.5; 536/23.6; 536/23.7; 536/23.74; 536/24.1
[58] Field of Search .................... 536/24.1, 23.1, 536/23.2, 23.5, 23.6, 23.7, 23.74; 435/320.1, 252.3, 252.33, 69.1, 71.1

[56] References Cited

U.S. PATENT DOCUMENTS

| | | | |
|---|---|---|---|
| 4,565,785 | 1/1986 | Gilbert et al. | 435/320.1 |
| 4,673,641 | 6/1987 | George et al. | 435/69.1 |
| 4,710,473 | 12/1987 | Morris | 435/320.1 |
| 4,738,921 | 4/1988 | Belagaje et al. | 435/69.7 |
| 4,795,706 | 1/1989 | Hsiung et al. | 435/252.33 |

FOREIGN PATENT DOCUMENTS

| | | |
|---|---|---|
| WO 94/12630 | 6/1994 | WIPO . |
| WO 94/12636 | 6/1994 | WIPO . |
| WO 96/10086 | 4/1996 | WIPO . |

OTHER PUBLICATIONS

Brosius and Holy (1984) *Proc. Nat'l. Acad. Sci. USA* 81: 6929–6933.

Amann et al. (1988) *Gene* 69: 301.

Poolman et al. (1990) *J. Bacteriol.* 172(7): 4037–4047.

Bouffard et al. (1994) *J. Mol. Biol.* 244: 269–278.

Peng et al. (1992) *J. Biochem.* 112: 604–608.

Maskell et al. (1992) *Mol. Microbiol.* 6(20): 3051–3063.

Adams et al. (1988) *J. Bacteriol.* 170(1): 203–212.

Fornwald et al. (1987) *Proc. Nat'l Acad. Sci. USA* 84: 2130–2134.

Graves et al. (1986) *J. Biol. Chem.* 261(24): 11409–11415.

Vieira and Messing (1982) *Gene* 19: 259–268.

Narimatsu et al. (1986) *Proc. Nat'l Acad. Sci. USA* 83: 4720–4724.

Dabkowski et al. (1993) *Transplant Proc.* 25: 2921.

Yamamoto et al. (1990) *Nature* 345: 229–233.

Gotschlich, E.C. (1994) *J. Exp. Med.* 180: 2181–2190.

Fusi et al. (1995) *Gene* 154: 99–103.

George et al., "Current methods in sequence comparison and analysis," in *Macromolecular Sequencing and Synthesis, Selected methods and Applications*, 1988, D.H. Schlesinger (ed.), Alan R. Liss, Inc. New York, NY, pp. 127–149.

*Primary Examiner*—Remy Yucel
*Attorney, Agent, or Firm*—Townsend and Townsend and Crew

[57] ABSTRACT

The present invention provides isolated recombinant nucleic acid constructs comprising a dual bacterial promoter operably linked to a heterologous nucleic acid which encodes a desired polypeptide. The constructs are useful for the expression of the desired polypeptides in bacterial cells at high levels.

48 Claims, 8 Drawing Sheets

Figure 2

```
        XbaI
GAAAAGAAGTCTAGANNNATGNNNNN....
 RBS       Met of recombinant gene
```

Fig. 5A.    Plasmid TGKS (blunt):

$$\text{GA}\underline{\text{AAAGA}}\text{AGT}\overset{\overline{\text{SrfI}}}{\text{CTAGCCCGGGC}}\text{TAGA}$$
      RBS Fig. 5B.    Plasmid pTGKS with recombinant insert:

GA<u>AAAGA</u>AGTCTAGCCC<u>ATG</u>NNNNNNN
   RBS         Met of recombinant gene

```
1                                                              58
*                                                               *
GTAAAGAAGTTATGGAGCNTCTTNGTCAGTAAAAAGTTATTTTTTTCAACAGCGTTCA
CATTTCTTCAATACCTCGNAGAANCAGTCATTTTTCAATAAAAAAGTTGTCGCAAGT 59                                                             116
*                         pPHO SEQ.                             *
TAAAGTGTCACGGCCGGAGAATTATAGTCGCTTGGTTTTTATTTTTTAAGTATTGGTA
ATTTCACAGTGCCGGCCTCTTAATATCAGCGAACCAAAAATAAAAAATTCATAACCAT 117                                                            174
*       ←pPHOX2 plasmid seq.┘ (XbaI)                            *
ACTAGTACGCAAGTTCACGTAAAAAGGGTAACTAGATAGACGANGGTCCGGNGTAGAG
TGATCATGCGTTCAAGTGCATTTTTCCCATTGATCTATCTGCTNCCAGGCCNCATCTC 175                                                            232
*                                                               *
GATCCGGGCTTATCGACTGCACGGTGCACCAATGCTTCTGGGTCAGGCAGCCATCGGA
CTAGGCCCGAATAGCTGACGTGCCACGTGGTTACGAAGACCCAGTCCGTCGGTAGCCT 233                                                            290
*                                                               *
AGCTGTGGTATGGCTGTGCAGGTCGTAAATCACTGCATAATTCGTGTCGCTCAAGGCG
TCGACACCATACCGACACGTCCAGCATTTAGTGACGTATTAAGCACAGCGAGTTCCGC 291                                                            348
*                                                               *
CACTCCCGTTCTGGATAATGTTTTTTGCGCCGACATCATAACGGTTCTGGCAAATATT
GTGAGGGCAAGACCTATTACAAAAAACGCGGCTGTAGTATTGCCAAGACCGTTTATAA 349                                                            406
*             -35   tac promoter     -10                        *
CTGAAATGAGCTGTTGACAATTAATCATCGGCTCCTATAATGTGTGGAATTGTGAGCG
GACTTTACTCGACAACTGTTAATTAGTAGCCGAGCATATTACACACCTTAACACTCGC 407                                                            464
*                                                               *
GATAACAATTTCACACAGGAAACAGAATTCCCGGGGATCCGTCGACCTGCAGCTAAAA
CTATTGTTAAAGTGTGTCCTTTGTCTTAAGGGCCCCTAGGCAGCTGGACGTCGATTTT 465                                                            522
*                                                               *
ATGCGGTAGCTTCTGATTATCCAAAATGCCAACTTTGTATGGAAAATGAAGGTTATTT
TACGCCATCGAAGACTAATAGGTTTTACGGTTGAAACATACCTTTTACTTCCAATAAA
```

FIG. 6-1.

```
523                                                         580
*                                                             *
GGGTCGCATTAATCACCCAGCCCGCAGCAATCACCGTGTTGTTCGTTTCCAAATGGAA
CCCAGCGTAATTAGTGGGTCGGGCGTCGTTAGTGGCACAACAAGCAAAGGTTTACCTT 581                                                         638
*                                                             *
GACAAGGAGTGGGGCTTCCAATACTCGCCTTATGCCTACTTTAACGAACATTCTATCT
CTGTTCCTCACCCCGAAGGTTATGAGCGGAATACGGATGAAATTGCTTGTAAGATAGA 639                                                         696
*                                                             *
TCTTTTATGGTAAGCACGAACCAATGCACATCAGTCCATTGACGTTTGGCCGTCTCCT
AGAAAATACCATTCGTGCTTGGTTACGTGTAGTCAGGTAACTGCAAACCGGCAGAGGA 697                                                         754
*                                                             *
AACAATTGTTGAAGCATTCCCCTGGTTACTTCGCAGGTTCAAATGCCGATCTTCCAAT
TTGTTAACAACTTCGTAAGGGGACCAATGAAGCGTCCAAGTTTACGGCTAGAAGGTTA 755                                                         812
*                                                             *
TGTAGGTGGTTCAATTCTTACACATGAACACTATCAAGGTGGTCGCCATACCTTCCCA
ACATCCACCAAGTTAAGAATGTGTACTTGTGATAGTTCCACCAGCGGTATGGAAGGGT 813                                                         870
*                                                             *
ATGGAAGTAGCAGGCATTAAAGAAAAAGTTAGCTTTGATGGTTACTCTGATGTTGAGG
TACCTTCATCGTCCGTAATTTCTTTTTCAATCGAAACTACCAATGAGACTACAACTCC 871                                                         928
*                                                             *
CTGGCATCGTTAATTGGCCTATGTCTGTTCTTCGTCTAAGAAGTGAAGACAAGGGAAG
GACCGTAGCAATTAACCGGATACAGACAAGAAGCAGATTCTTCACTTCTGTTCCCTTC 929                                                         986
*                                                             *
ACTTATCGCTCTTGCAACTAAAATCCTAAATTGCTGGCGTGGTTATTCAGACGAAAAA
TGAATAGCGAGAACGTTGATTTAGGATTTAACGACCGCACCAATAAGTCTGCTTTTT 987                                                        1044
*                                                             *
GCTGGGGTCTTGGCTGAGTCTGATGGACAACCTCACCACACCATTACTCCAATTGCTC
CGACCCCAGAACCGACTCAGACTACCTGTTGGAGTGGTGTGGTAATGAGGTTAACGAG
```

FIG. 6-2.

```
1045                                                           1102
*                                                                 *
GTAGAAAAGACGGCAAATTTGAATTGGATTTGGTTCTTCGTGACAATCAAACTTCTGA
CATCTTTTCTGCCGTTTAAACTTAACCTAAACCAAGAAGCACTGTTAGTTTGAAGACT 1103                                                           1160
*                                                                 *
AGAATATCCAGACGGTATCTATCACCCACATAAAGATGTTCAACATATTAAGAAAGAA
TCTTATAGGTCTGCCATAGATAGTGGGTGTATTTCTACAAGTTGTATAATTCTTTCTT 1161                                                           1218
*                                                                 *
AATATTGGTTTGATTGAAGTTATGGGATTGGCCATTCTTCCACCTCGTTTGAAAACAG
TTATAACCAAACTAACTTCAATACCCTAACCGGTAAGAAGGTGGAGCAAACTTTTGTC 1219                                                           1276
*                                                                 *
AACTTAAAGATGTTGAAGATTATCTATTAGGTCAAGGTAACCAAGTTGCTCCAATTCA
TTGAATTTCTACAACTTCTAATAGATAATCCAGTTCCATTGGTTCAACGAGGTTAAGT 1277                                                           1334
*                                                                 *
CCAAGAATGGGCAGATGAACTCAAAGCTCAAATCCGAATATTACGGCTGAGGAAGTGA
GGTTCTTACCCGTCTACTTGAGTTTCGAGTTTAGGCTTATAATGCCGACTCCTTCACT 1335                                                           1392
*                                                                 *
CAGAAGTTGTTCGACAATCTGTTGCAGATATCTTTGCTCGTGTACTAGAAGATGCAGG
GTCTTCAACAAGCTGTTAGACAACGTCTATAGAAACGAGCACATGATCTTCTACGTCC 1393                                                           1450
*                                                        ┌galEpromoter*
                                                         │ -35
TGTTTATAAGACTAATAGTGAAGGCTTGGATCAGTTTAAAGCATT TGTAGA TTTTGTA
ACAAATATTCTGATTATCACTTCCGAACCTAGTCAAATTTCGTAA ACATCT AAAACAT 1451                                                           1508
*                                                                 *
       -10                    RBS      XbaI
AATTTAGCTGA TTAATT GTTTTTTCTGAAGAA GGAGG TCTAGA GTCGACCTGCAGGC
TTAAATCGACT AATTAA CAAAAAAGACTTCTT CCTCC AGATCT CAGCTGGACGTCCG
```

FIG. 6-3.

1509                                                                        1560
*                                                                             *
    HDIII
ATGCAAGCTTCTGTTTTGGCGGATGAGAGAAGATTTTCAGCCTGATACAGATT
TACGTTCGAAGACAAAACCGCCTACTCTCTTCTAAAAGTCGGACTATGTCTAA
——pPHOX2 SEQUENCE——

*FIG. 6-4.*

EXPRESSION VECTORS

CROSS REFERENCE TO RELATED APPLICATIONS

This application is a continuation-in-part of U.S. Provisional Application No. 60/029,545, filed Nov. 8, 1996, which is incorporated herein by reference.

FIELD OF THE INVENTION

The present invention relates to improved vectors and fermentation protocols for expression of recombinant proteins in bacterial cells. The invention can be used for expression of any desired protein, including enzymes useful in the enzymatic synthesis of oligosaccharides.

BACKGROUND OF THE INVENTION

The production of biologically active polypeptides and proteins is important economically for the manufacture of human and animal pharmaceutical formulations, enzymes, and other specialty chemicals. Recombinant DNA techniques using bacterial, fungal, mammalian, or insect cells as expression hosts are particularly useful means for producing large quantities of polypeptides.

Recombinant production of desired proteins generally involves transfecting host cells with an expression vector that contains signals which, when operably linked to a gene encoding the protein, control expression of the gene. The cells are grown under conditions suitable for expression of the recombinant protein. The expression control signals typically include a promoter, which influences the rate at which a gene located downstream of the promoter is transcribed into RNA and determines the transcriptional start site. Expression control signals are chosen so as to be functional in the host cell used for production of the desired protein. For instance, the bacterium E. coli is commonly used to produce recombinant proteins in high yields. Numerous references disclose methods of using E. Coli and other bacteria to produce proteins recombinantly. (see, e.g., U.S. Pat. Nos. 4,565,785; 4,673,641; 4,738,921; 4,795,706; and 4,710,473).

For recombinantly produced proteins that are intended for commercial use, in particular, it is desirable to obtain a high level of expression of the desired protein from the host cells. Increasing the amount of desired protein produced per cell can reduce costs of production due to the decreased volume of cells that must be grown to obtain a given amount of product, and also can facilitate purification because the desired product makes up a larger percentage of the total protein produced by the host cells. Therefore, a need exists for expression control signals that are capable of expressing a desired protein at high levels. The present invention fulfills this and other needs.

SUMMARY OF THE INVENTION

The present invention provides isolated recombinant nucleic acid constructs that comprise a dual bacterial promoter operably linked to a heterologous nucleic acid that encodes a desired polypeptide. The constructs are useful for expressing a desired polypeptide in bacterial host cells at high levels. The dual promoters comprise a first component derived from a tac-related promoter and a second promoter component obtained from a bacterial gene or operon that encodes an enzyme or enzymes involved in galactose metabolism. A number of galactose promoters can be used as the second promoter component; an exemplary promoter is a UDPgalactose-4-epimerase (also known as UDPglucose-4-epimerase) promoter such as that derived from Streptococcus thermophilus.

Also provided by the invention are expression vectors which include a dual bacterial promoter operably linked to a heterologous nucleic acid that encodes a desired polypeptide. The expression vectors can further comprise other components such as a selectable marker. The constructs can also comprise an origin of replication sequence that functions in E. coli or other host cell. A preferred construct of the invention, the plasmid pTGK (described in detail below) was deposited with the American Type Culture Collection under Accession No. 98059 on May 22, 1996.

The invention also provides a bacterial cell that contains a recombinant expression cassette that includes the dual bacterial promoter unit operably linked to a heterologous nucleic acid. The expression cassette can be integrated into the genome of the host cell or be present on an independently replicating plasmid. A preferred bacterial cell is E. coli.

The invention further provides methods of making a desired polypeptide. The methods involve culturing in an appropriate medium bacterial cells that contain a recombinant expression cassette having a dual bacterial promoter unit operably linked to a heterologous nucleic acid under conditions that allow expression of the heterologous nucleic acid. Typically E. coli are used as the host cell. The methods and constructs can be used to express a wide variety of polypeptides in bacterial cells. Exemplary polypeptides include hormones, growth factors, and the like, as well as enzymes useful in the synthesis of carbohydrates. Such enzymes include CMP-sialic acid synthetase, UDP-glucose pyrophosphorylase, adenylate kinase, pyruvate kinase, sialic acid aldolase, UDP-GlcNAc pyrophosphorylase, and myokinase, galactosyltransferase, and N-acetyl glucosaminyltransferase.

BRIEF DESCRIPTION OF THE DRAWINGS

FIG. 2 shows the spacing between the ribosome binding site (Shine-Dalgarno sequence) and the initiation codon of the recombinant gene in the vectors of the invention (SEQ ID NO:2).

FIGS. 5A and 5B show that one can maintain optimal spacing between the ribosome binding site and the initiation codon of the gene to be expressed in vectors of the invention by amplifying the DNA to be expressed using as primers oligonucleotides that begin with the ATG initiation codon. FIG. 5A shows the relationship between the ribosome binding site (RBS) and the SrfI restriction site in the plasmid pTGKS (SEQ ID NO:3). Digestion with SrfI leaves a blunt end to which a blunt-ended recombinant gene that begins with the ATG initiation codon can be ligated as shown in FIG. 5B (SEQ ID NO:4).

FIG. 6 shows the nucleotide sequence of one embodiment of a dual tac-gal promoter of the invention, flanked by pPHOX2 sequences, as indicated (SEQ ID NO:1). The −35 and −10 consensus sequences of both the tac and galE promoters are shown, as are the locations of XbaI and HindIII sites which are useful for inserting a recombinant gene for expression.

DETAILED DESCRIPTION OF THE INVENTION

Figure 1:
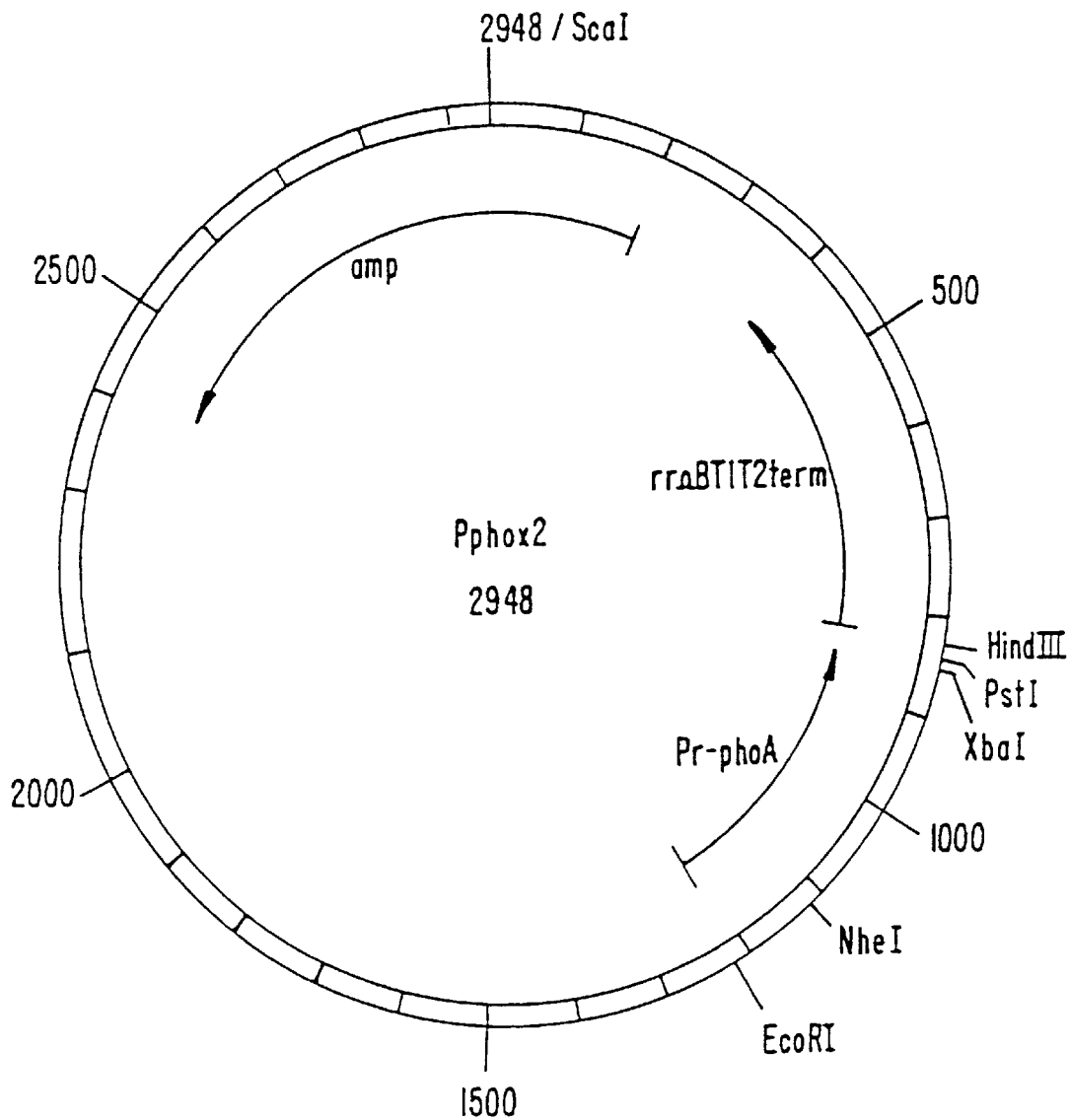
FIG. 1 is a map of the plasmid pPHOX2.

The present invention provides improved promoters and vectors for the recombinant expression of desired polypeptides. The promoters and vectors of the invention are particularly suited for the expression of recombinant proteins in bacterial hosts, such as *E. coli*. Also provided are fermentation protocols for obtaining high levels of recombinant protein expression using the promoters and vectors of the invention.

Definitions

Much of the nomenclature and general laboratory procedures required in this application can be found in Sambrook et al., *Molecular Cloning: A Laboratory Manual* (2nd Ed.), Vol. 1–3, Cold Spring Harbor Laboratory, Cold Spring Harbor, N.Y., 1989. The manual is hereinafter referred to as "Sambrook et al."

Unless defined otherwise, all technical and scientific terms used herein have the same meaning as commonly understood by one of ordinary skill in the art to which this invention belongs. Singleton et al. (1994) *Dictionary of Microbiology and Molecular Biology,* second edition, John Wiley and Sons (New York) provides one of skill with a general dictionary of many of the terms used in this invention. Although any methods and materials similar or equivalent to those described herein can be used in the practice or testing of the present invention, the preferred methods and materials are described. For purposes of the present invention, the following terms are defined below.

The term "nucleic acid" refers to a deoxyribonucleotide or ribonucleotide polymer in either single- or double-stranded form, and unless otherwise limited, encompasses known analogues of natural nucleotides that hybridize to nucleic acids in manner similar to naturally occurring nucleotides. Unless otherwise indicated, a particular nucleic acid sequence includes the complementary sequence thereof.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The term "recombinant" when used with reference to a cell indicates that the cell replicates a heterologous nucleic acid, or expresses a peptide or protein encoded by a heterologous nucleic acid. Recombinant cells can express genes that are not found within the native (non-recombinant) form of the cell. Recombinant cells can also express genes that are found in the native form of the cell, but wherein the genes are modified and re-introduced into the cell by artificial means.

A "heterologous sequence" or a "heterologous nucleic acid", as used herein, is one that originates from a foreign source (or species) or, if from the same source, is modified from its original form. Thus, a heterologous nucleic acid operably linked to a promoter is from a source different from that from which the promoter was derived, or, if from the same source, is modified from its original form. For example, a UDPglucose 4-epimerase gene promoter can be linked to a structural gene encoding a polypeptide other than native UDPglucose 4-epimerase. Modification of the heterologous sequence may occur, e.g., by treating the DNA with a restriction enzyme to generate a DNA fragment that is capable of being operably linked to the promoter. Techniques such as site-directed mutagenesis are also useful for modifying a heterologous sequence.

A "recombinant expression cassette" or simply an "expression cassette" is a nucleic acid construct, generated recombinantly or synthetically, with nucleic acid elements that are capable of affecting expression of a structural gene in hosts that are compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter (e.g., a dual promoter that contains a tac promoter component and a gal promoter component). Additional factors necessary or helpful in effecting expression may also be used as described herein. For example, an expression cassette can also include nucleotide sequences that encode a signal sequence that directs secretion of an expressed protein from the host cell.

The term "isolated" is meant to refer to material which is substantially or essentially free from components which normally accompany the material as found in its native state. Thus, an isolated protein, for example, does not include materials normally associated with their in situ environment. Typically, isolated proteins of the invention are at least about 80% pure, usually at least about 90%, and preferably at least about 95% pure as measured by band intensity on a silver stained gel or other method for determining purity. In the present invention polypeptides are purified from transgenic cells.

UDPglucose-4-epimerase (E.C. 5.1.3.2) is also known as UDPgalactose-4-epimerase and phosphoribulose epimerase. These terms are used interchangeably herein.

Two polynucleotides or polypeptides are said to be "identical" if the sequence of nucleotides or amino acid residues in the two sequences is the same when aligned for maximum correspondence. Optimal alignment of sequences for comparison may be conducted by the local homology algorithm of Smith and Waterman, *Adv. Appl. Math.* 2:482 (1981), by the homology alignment algorithm of Needleman and Wunsch, *J. Mol. Biol.* 48:443 (1970), by the search for similarity method of Pearson and Lipman *Proc. Natl. Acad. Sci. (U.S.A.)* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The term "substantial identity" as applied to polypeptides means that a polypeptide comprises a sequence that is at least 80% identical, preferably 90%, more preferably 95% or more, to a reference sequence over a comparison window of about 20 residues to about 600 residues—typically about 50 to about 500 residues usually about 250 to 300 residues. The values of percent identity are determined using the programs above.

The terms "substantial identity" or "substantial sequence identity" as applied to nucleic acid sequences and as used herein denote a characteristic of a polynucleotide sequence, wherein the polynucleotide comprises a sequence that has at least 85 percent sequence identity, preferably at least 90 to 95 percent sequence identity, and more preferably at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

Another indication that nucleotide sequences are substantially identical is if two molecules hybridize to each other under stringent conditions. Stringent conditions are sequence-dependent and will be different in different circumstances. Generally, stringent conditions are selected to be about 5° to about 20° C., usually about 10° C. to about 15° C., lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. For instance in a standard Southern hybridization procedure, stringent conditions will include an initial wash in 6×SSC at 42° C. followed by one or more additional washes in 0.2×SSC at a temperature of at least about 55° C., typically about 60° C. and often about 65° C.

Nucleotide sequences are also substantially identical for purposes of this invention when the polypeptides which they encode are substantially identical. Thus, where one nucleic acid sequence encodes essentially the same polypeptide as a second nucleic acid sequence, the two nucleic acid sequences are substantially identical, even if they would not hybridize under stringent conditions due to silent substitutions permitted by the genetic code (see, Darnell et al. (1990) *Molecular Cell Biology,* Second Edition *Scientific American Books* W. H. Freeman and Company New York for an explanation of codon degeneracy and the genetic code).

Protein purity or homogeneity can be indicated by a number of means well known in the art, such as polyacrylamide gel electrophoresis of a protein sample, followed by visualization upon staining. For certain purposes high resolution will be needed and HPLC or a similar means for purification utilized.

The practice of this invention involves the construction of recombinant nucleic acids and the expression of genes in transfected bacterial cells. Molecular cloning techniques to achieve these ends are known in the art. A wide variety of cloning and in vitro amplification methods suitable for the construction of recombinant nucleic acids such as expression vectors are well-known to persons of skill. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); and *Current Protocols in Molecular Biology,* F. M. Ausubel et al., eds., Current Protocols, a joint venture between Greene Publishing Associates, Inc. and John Wiley & Sons, Inc., (1994 Supplement) (Ausubel).

Examples of protocols sufficient to direct persons of skill through in vitro amplification methods, including the polymerase chain reaction (PCR) the ligase chain reaction (LCR), Qβ-replicase amplification and other RNA polymerase mediated techniques are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem.* 35, 1826; Landegren et al., (1988) *Science* 241, 1077–1080; Van Brunt (1990) *Biotechnology* 8, 291–294; Wu and Wallace, (1989) *Gene* 4, 560; and Barringer et al. (1990) *Gene* 89, 117. Improved methods of cloning in vitro amplified nucleic acids are described in Wallace et al., U.S. Pat. No. 5,426,039.

DESCRIPTION OF THE INVENTION

The invention provides expression cassettes that are useful for expressing recombinant genes in bacterial cells, such as *E. coli,* at high levels. Also provided are vectors that include the expression cassettes, as well as fermentation protocols for using the expression cassettes to obtain expression of a desired heterologous protein. The expression cassettes of the invention contain a dual promoter operably linked to a heterologous nucleic acid that encodes a desired gene product, typically a polypeptide. The dual promoters include a tac promoter component linked to a promoter component obtained from a gene or genes that encode enzymes involved in galactose metabolism (e.g., a promoter from a UDPgalactose 4-epimerase gene (galE)). The dual tac-gal promoter provides a level of expression that is greater than that provided by either promoter alone. The dual promoter can have a synergistic effect, having a greater than additive effect on expression level.

To obtain high level expression of a cloned gene, the expression cassettes can include other sequences such as ribosome binding sites for translational initiation and transcription/translation terminator sequences. To allow selection of cells comprising the constructs, one or more selectable marker genes (e.g., antibiotic-resistance genes) are conveniently included in the expression vectors. The vectors may comprise other sequences to allow the vector to be cloned in prokaryotic hosts, such as a broad host range prokaryote origin of replication. One of skill will recognize that each of these vector components can be modified without substantially affecting their function.

One component of the dual promoters of the invention is a tac promoter, which is a combination of the lac and trp promoters. An example of an expression vector that contains the tac promoter is pKK223-3 (Brosius and Holy, *Proc. Nat'l. Acad. Sci. USA* 81: 6929 (1984)); this vector is commercially available (Pharmacia Biotech, Inc., Piscataway N.J.). Variants of the tac promoter, such as trc (Amann et al., *Gene* 69: 301 (1988), are also useful as a first component of the claimed dual promoters.

A second component of the dual promoters of the invention is a promoter obtained from a gene or genes that encode enzymes involved in galactose metabolism. In bacteria, such genes are often clustered, with more than one gal gene present in close proximity to others. For example, in *Streptococcus thermophilus* the genes encoding UDPgalactose-4-epimerase (galE; also known as UDPglucose-4-epimerase) and aldose 1-epimerase (mutarotase) (galM) are closely linked (Poolman et al., *J. Bacteriol* 172:4037–4047 (1990)). In *E. coli,* four gal genes are linked (galE, galT (UDPglucose-hexose-1-phosphate uridylyltransferase), galK (galactokinase), and galM) (Bouffard et al., *J. Mol. Biol.* 244: 269–278 (1994)). Similarly, the gal operon of *Klebsiella pneumoniae* also includes several genes (in the order galE, galT, and galK) (Peng et al., *J. Biochem.* 112: 604–608 (1992)), while that of *Hemophilus influenzae* includes, in order, galT, galK, and galM in a single operon (Maskell et al., *Mol. Microbiol.* 6: 3051–3063 (1992)) and the gal operon of *Streptomyces lividans* has the gene order galT, galE, galK (Adams et al., *J. Bacteriol.* 170) 203–212 (1988)). Galactose operons are expressed under the control of one or more promoters. For example, the *S. lividans* gal operon includes two promoters, one (galP1) that is galactose-inducible and directs transcription of the galT, galE, and galK genes and a second promoter (galP2) that is located within the operon just upstream of the galE gene and is constitutively expressed (Fornwald et al., *Proc. Nat'l. Acad. Sci. USA* 84: 2130–2134 (1987)). The *E. coli* gal operon also includes, in addition to an inducible promoter, a constitutive promoter positioned upstream of the galE gene (Id.).

In a preferred embodiment, the dual promoter includes a promoter from a bacterial UDPgalactose 4-epimerase (galE) gene. The *Streptococcus thermophilus* UDPgalactose 4-epimerase gene described by Poolman et al. (*J. Bacteriol* 172: 4037–4047 (1990)) is a particular example of a gene from which one can obtain a promoter that is useful in the present invention. Promoters from UDPglucose 4-epimerase genes of other organisms can be used in the present invention, so long as the promoters function in *E. coli* or other desired bacterial host cell. Exemplary organisms that have genes encoding UDPglucose 4-epimerase include *E. coli, K. pneumoniae, S. lividans,* and *E. stewartii,* as well as Salmonella and Streptococcus species.

The isolation of gal genes and their promoters may be accomplished by a number of techniques well known to those skilled in the art. For instance, oligonucleotide probes that selectively hybridize to the exemplified UDPglucose 4-epimerase gene or promoter described below can be used to identify the desired gene in DNA isolated from another organism. The use of such hybridization techniques for identifying homologous genes is well known in the art and need not be described further. The promoters obtained are typically identical to or show substantial sequence identity to the exemplary glucose epimerase promoter described below.

Alternatively, polynucleotides having the nucleotide sequence of the desired promoter fragments can be synthesized by well-known techniques as described in the technical literature. See, e.g., Carruthers et al., *Cold Spring Harbor Symp. Quant. Biol.* 47:411–418 (1982), and Adams et al., *J. Am. Chem. Soc.* 105:661 (1983). One can then obtain double stranded DNA fragments either by synthesizing the complementary strand and annealing the strands together under appropriate conditions, or by adding the complementary strand using DNA polymerase with an appropriate primer sequence.

The tac and gal promoters that comprise the dual promoters of the invention can be identical to the corresponding promoters in the wild-type bacterial cells, or can be modified as desired, such as by insertion, deletion, or substitution of nucleotides. Such modifications will maintain those portions of the promoter sequences that are necessary for promoter function. For example, the −10 and −35 consensus sequences for promoters of gram-positive and gram-negative bacteria (see, e.g., Graves et al.,*J. Biol. Chem.* 261: 11409–11415 (1986); Singer and Berg, *Genes & Genomes,* University Science Books, Mill Valley, Calif., 1991, pp. 140–143) will be maintained to the extent necessary to obtain expression. Nucleotides that are important for proper function of a promoter in *E. coli* are shown, for example, in Singer and Berg at page 143. Regions of the promoter sequences that are not essential to promoter function can be modified as desired, for example, to facilitate cloning by inserting a restriction site adjacent to or within the promoter regions.

Both the tac and the gal promoter components will generally have a binding site for the cAMP receptor protein (CRP, which is the product of the crp gene). cAMP is widely known as a signal for carbon source availability, with its levels being inversely correlated with the energetic state of the cell as evidenced by growth of cells on poor carbon sources (e.g., fructose, glycerol, acetate) eliciting higher cAMP levels than growth on a good carbon source (e.g., glucose). cAMP regulates gene expression by binding to CRP. This high affinity binding produces a conformational change in the dimeric complex, which can then bind to a specific DNA site upstream of the binding site of RNA polymerase. Transcription is activated by accelerating the initial binding (increasing $K_B$) of the $E_o^{70}$ form of RNA polymerase, at least in the case of the gal operon.

The tac promoter component of the dual promoters of the invention is generally located upstream of the gal promoter component. Generally, the two promoter components are separated by about 0.1 to 2 kb of DNA. More preferably, about 0.5 to 1.5 kb separate the two promoter components. In a most preferred embodiment, the tac promoter component is located about 1 kb upstream of the gal promoter component. The source of the DNA separating the two promoter components is not particularly critical, so long as the DNA does not contain sequences that interfere with gene expression, such as transcription terminators. For example, in one embodiment the tac promoter component is separated from the gal promoter component by DNA obtained from the native 5' flanking region of the gal promoter component. In a preferred embodiment, about one kb of DNA from the 5' flanking region of the *S. thermophilus* galE gene separate the tac promoter component from the gal promoter component.

The nucleotide sequence of a preferred dual promoter is shown in SEQ ID NO:1. As shown, the dual promoter is inserted into the XbaI site of the pPHOX2 expression vector, destroying the upstream XbaI site. Nucleotides 1–146 and 1490–1561 of the sequence are from pPHOX2. The −35 and −10 consensus sequences of the tac promoter are at nucleotides 362–367 and 384–389, respectively. The galE promoter consensus sequences are at nucleotides 1438–1443 (−35) and 1462–1467 (−10). A ribosome binding site (RBS) is found at nucleotides 1483–1488. To facilitate insertion of a gene to be expressed downstream of the dual promoter, the RBS is followed by an XbaI restriction site and a HindIII site is present in the pPHOX2 sequence just 3' of the XbaI site.

The vectors of the invention can also contain a nucleic acid sequence that enables the vector to replicate independently in one or more selected host cells. Generally, this sequence is one that enables the vector to replicate independently of the host chromosomal DNA, and includes origins of replication or autonomously replicating sequences. Such sequences are well known for a variety of bacteria. For instance, the origin of replication from the plasmid pBR322 is suitable for most Gram-negative bacteria.

The vectors also comprise selectable marker genes to allow selection of bacterial cells bearing the desired construct. These genes encode a protein necessary for the survival or growth of transformed host cells grown in a selective culture medium. Host cells not transformed with the vector containing the selection gene will not survive in the culture medium. Typical selection genes encode proteins that confer resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media, e.g., the gene encoding D-alanine racemase for Bacilli. A number of selectable markers are known to those of skill in the art and are described for instance in Sambrook et al., supra. A preferred selectable marker for use in using the dual tac-lac promoter to express a desired polypeptide is a kanamycin resistance marker (Vieira and Messing, Gene 19: 259 (1982)). Use of kanamycin selection is advantageous over, for example, ampicillin selection because ampicillin is quickly degraded by β-lactamase in culture medium, thus removing selective pressure and allowing the culture to become overgrown with cells that do not contain the vector.

Construction of suitable vectors containing one or more of the above listed components employs standard ligation techniques as described in the reference cited above. Isolated plasmids or DNA fragments are cleaved, tailored, and re-ligated in the form desired to generate the plasmids required. To confirm correct sequences in plasmids constructed, the plasmids are analyzed by standard techniques such as by restriction endonuclease digestion, and/or sequencing according to known methods.

A number of bacterial host cells can be used with the vectors of the invention. Examples of useful bacteria include Escherichia, Enterobacter, Azotobacter, Erwinia, Bacillus, Pseudomonas, Klebsielia, Proteus, Salmonella, Serratia, Shigella, Rhizobia, Vitreoscilla, and Paracoccus. Suitable E. coli hosts include the following strains: JM101, RR1, DH5$_\alpha$, and others. These examples are illustrative rather than limiting. Depending on the host cell used, transformation is done using standard techniques appropriate to such cells. Suitable techniques include calcium treatment employing calcium chloride, polyethylene glycol, or electroporation.

The invention also provides methods for using the dual tac-gal promoters to obtain high level expression of a desired polypeptide. Host cells are transformed with vectors containing the dual promoter expression cassettes and cultured in culture medium under conditions appropriate for expression of the desired polypeptide. The cells can be grown in shake flasks or other containers, although for large-scale preparation of the polypeptide growth in a fermentor is preferred. To obtain the maximum level of expression, galactose is added to the nutrient medium at an appropriate time in the growth cycle to induce increased expression of the desired polypeptide. For example, growth of the host cells can be initiated in culture medium containing fructose (0.25% final concentration) as the carbon source; other sugars (e.g., glycerol, acetate) that cause an increase in intracellular cAMP (adenosine 3',5'-cyclic monophosphate) concentration can also be used as a carbon source. Approximately 5–6 hours after the culture is initiated, or once the cells have reached an appropriate density (ca. 3–6 $A_{600}$), a solution of fructose and galactose (final concentration 3% fructose, 0.6% galactose) is added to the medium (in fed-batch mode for a fermentor). The galactose increases the level of expression from the dual tac-gal promoter expression cassettes of the invention. The feed rate of fructose/galactose solution can be increased during the growth cycle (in a stepped or ramped fashion) as the culture becomes dense with cell growth. Preferably, fructose/galactose solution is fed through the end of the growth cycle.

The dual promoters of the invention are useful for expression of any desired polypeptide or protein at very high yields. The polypeptides may be homologous to the bacterial host cell, or preferably, are heterologous to the host cell. For example, one can express yeast, fungal, mammalian, and plant proteins at very high levels using the dual promoters. Many polypeptides produced using the claimed dual promoters will be enzymatically active. Although certain polypeptides, such as those that require glycosylation or other eukaryote-specific processing for activity, may not be produced in active form in bacterial host cells, the inactive polypeptides nevertheless find use as, for example, immunogens for induction of antibodies, molecular weight markers, and the like. Exemplary bacterial polypeptides that one can express using the dual promoters include β-lactamase, carbohydrate metabolizing enzymes, alkaline phosphatase, restriction enzymes, DNA and RNA polymerases, ligases, kinases, endo- and exonucleases, and the like. Exemplary fungal polypeptides include ligninases, proteases, glycosyltransferases, and the like. Exemplary mammalian polypeptides that one can express in bacterial host cells using the claimed dual promoters include hormones such as insulin, growth hormones (including human growth hormone and bovine growth hormone), tissue-type plasminogen activator (t-PA), renin, clotting factors such as factor VIII and factor IX, bombesin, thrombin, hemopoietic growth factor, serum albumin, receptors for hormones or growth factors, interleukins, colony stimulating factors, T-cell receptors, MHC polypeptides, viral antigens, glycosyltransferases, and the like. This list of enzymes is exemplary, not exclusive, as the dual promoters of the invention are useful for obtaining transcription of any nucleic acid expression unit that is operably linked to the dual promoters. Such expression units include not only those that encode polypeptides, but also those for which the desired product is a nucleic acid, for example, an antisense RNA.

The vectors are particularly useful for expressing enzymes that are useful in the enzymatic synthesis of carbohydrates. The use of enzymatic synthesis of carbohydrate offers advantages over chemical methods due to the virtually complete stereoselectivity and linkage specificity offered by enzymes (Ito et al., Pure Appl. Chem., 65:753 (1993); U.S. Pat. Nos. 5,352,670, and 5,374,541). A number of glycosyltransferase cycles (for example, sialyltransferase cycles, galactosyltransferase cycles, and fucosyltransferase cycles) are described in U.S. Pat. No. 5,374,541 and WO 9425615 A. Other glycosyltransferase cycles are described in Ichikawa et al. J. Am. Chem. Soc. 114:9283 (1992), Wong et al., J. Org. Chem. 57: 4343 (1992), DeLuca et al., J. Am. Chem. Soc. 117:5869–5870 (1995), and Ichikawa et al. in Carbohydrates and Carbohydrate Polymers. Yaltami, ed. (ATL Press, 1993). Exemplary enzymes useful in the synthesis of carbohydrates that one can express using the claimed dual promoters also include CMP-sialic acid synthetase, UDP-glucose pyrophosphorylase, adenylate kinase, pyruvate kinase, sialic acid aldolase, UDP-GlcNAc pyrophosphorylase, myokinase, galactosyltransferases, glycosyltransferases encoded by the los locus of Neisseria gonorrhoeae (see, e.g., international application WO 96/10086) and N-acetyl glucosaminyltransferases. Any of the enzymes described in these references and used in these cycles can be recombinantly expressed using the vectors of the invention.

A typical example of a glycosyltransferase cycle for which the required enzymes can be produced using the claimed dual tac-gal promoters is a galactosyltransferase cycle. The reaction medium for a galactosyltransferase cycle will preferably contain, in addition to a galactosyltransferase, donor substrate, acceptor sugar and divalent metal cation, a donor substrate recycling system comprising at least 1 mole of glucose-1-phosphate per each mole of acceptor sugar, a phosphate donor, a kinase capable of transferring phosphate from the phosphate donor to nucleoside diphosphates, and a pyrophosphorylase capable of forming UDP-glucose from UTP and glucose-1-phosphate and catalytic amounts of UDP and a UDPgalactose-4-epimerase. A galactosyltransferase is the principal enzyme in this cycle. Exemplary galactosyltransferases include β(1,3) galactosyltransferase, β(1,4) galactosyltransferase (E.C. No. 2.4.1.90, see, e.g., Narimatsu et al., *Proc. Nat'l. Acad. Sci. USA* 83: 4720–4724 (1986)), α(1,3) galactosyltransferase (E.C. No. 2.4.1.151, see, e.g., Dabkowski et al., *Transplant Proc.* 25:2921 (1993) and Yamamoto et al. *Nature* 345:229–233 (1990)) and α(1,4) galactosyltransferase (E.C. No. 2.4.1.38). Other enzymes used in the galactosyltransferase cycle include a kinase (for example, pyruvate kinase), an epimerase (for example, UDP-galactose-4-epimerase), and a pyrophosphorylase (for example, glucose pyrophosphorylase). DNA encoding all of these enzymes can be expressed using the vectors of the invention.

In some embodiments, the DNA encoding the polypeptide of interest may be expressed as a fusion with another polypeptide, preferably a signal sequence or other polypeptide having a specific cleavage site at the N-terminus of the mature polypeptide. In general, the signal sequence may be a component of the vector, or it may be a part of the polypeptide DNA that is inserted into the vector. The heterologous signal sequence selected should be one that is recognized and processed (i.e., cleaved by a signal peptidase) by the host cell. For bacterial host cells that do not recognize and process the native polypeptide signal sequence, the signal sequence is substituted by a bacterial signal sequence. A signal sequence can facilitate purification of the desired polypeptide by directing secretion of the desired protein from the cell into the extracellular medium.

The polypeptides produced by prokaryote cells may not necessarily fold properly. During purification from *E. coli*, the expressed polypeptides may first be denatured and then renatured. This can be accomplished by solubilizing the bacterially produced proteins in a chaotropic agent such as guanidine HCl and reducing all the cysteine residues with a reducing agent such as beta-mercaptoethanol. The polypeptides are then renatured, either by slow dialysis or by gel filtration. U.S. Pat. No. 4,511,503.

Detection of expressed polypeptides is achieved by methods known in the art as radioimmunoassays, Western blotting techniques, immunoprecipitation, or activity assays. Purification from *E. coli* can be achieved following procedures described in U.S. Pat. No. 4,511,503.

EXAMPLES

The following examples are offered to illustrate, but not to limit the present invention.

Example 1

Construction of pTGK

Construction of pPHOX2/galE

Plasmid pPHOX2 (FIG. 1) comprises a phosphate-starvation inducible promoter of the alkaline phosphatase gene (phoA), which increases transcription of genes under its control when phosphate levels become extremely low. This plasmid contains a phoA promoter as described in WO 94/12636, as well as a rrnB ribosomal terminator (obtained from pKK223-3, Pharmacia Biotech). The galactose-inducible promoter from the UDP-galactose-4-epimerase gene (galE) of *Streptococcus thermophilus* (Poolman et al., *J. Bacteriol.* 172:4037–4047 (1990)) and the tac promoter were inserted into pPHOX2.

The expression plasmid pTGK was constructed as follows. First, a fragment of the plasmid pHP1/tac (described in Poolman et al., *J. Bacteriol.* 172:4037–4047 (1990)) was amplified by polymerase chain reaction (PCR) using Pfu polymerase and XbaI primers at the 5' and 3' ends. The amplified fragment contained a tac promoter approximately one kb upstream of the galactose-inducible promoter from the UDPgalactose-4-epimerase gene (galE) of *Streptococcus thermophilus* (Poolman et al., supra.). The 5' primer (5'-GCTCTAGACGATCCGTCCGGCGTA-3'; (SEQ ID NO:5)) was designed to hybridize to the pBR322 vector region upstream of the promoter on pHP1/tac, while the 3' primer (5'-ATTCTAGACCTCCTTTCTCAGAAAAAACAATT-3'; (SEQ ID NO:6)) was designed to hybridize to a sequenced region of the galE promoter containing the Shine-Dalgarno ribosome binding site. The optimal spacing between the galE ribosome binding site and the initiation codon of the recombinant gene was maintained (FIG. 2). This amplified 1.3 kb DNA fragment, which encompassed both the tac and galE promoters, was digested with XbaI and inserted into XbaI-digested pPHOX2 (FIG. 1), which comprises a phosphate-starvation inducible promoter of the alkaline phosphatase gene (phoA, described in WO 94/12636), as well as a rrnB ribosomal terminator (obtained from pKK223-3, Pharmacia Biotech). The orientation of the dual tac-galE promoter was checked by BamHI digestion. The resulting plasmid is called pPHOX2/galE.

Addition of a Kanamycin Resistance Gene pPHOX2 has an ampicillin-resistance gene encoded by β-lactamase. Ampicillin is added to the culture to maintain the plasmid, but it is quickly degraded by β-lactamase, losing its effectiveness. In cells with a strong selective pressure against making the recombinant protein (e.g., as with CMP-sialic acid synthetase), overgrowth of cells without the plasmid can occur. To alleviate this problem, the plasmid was re-engineered to include a kanamycin resistance (Kan$^r$) gene, which gives a stronger selection since the encoded protein acts at the level of the membrane transport system.

Figure 3:
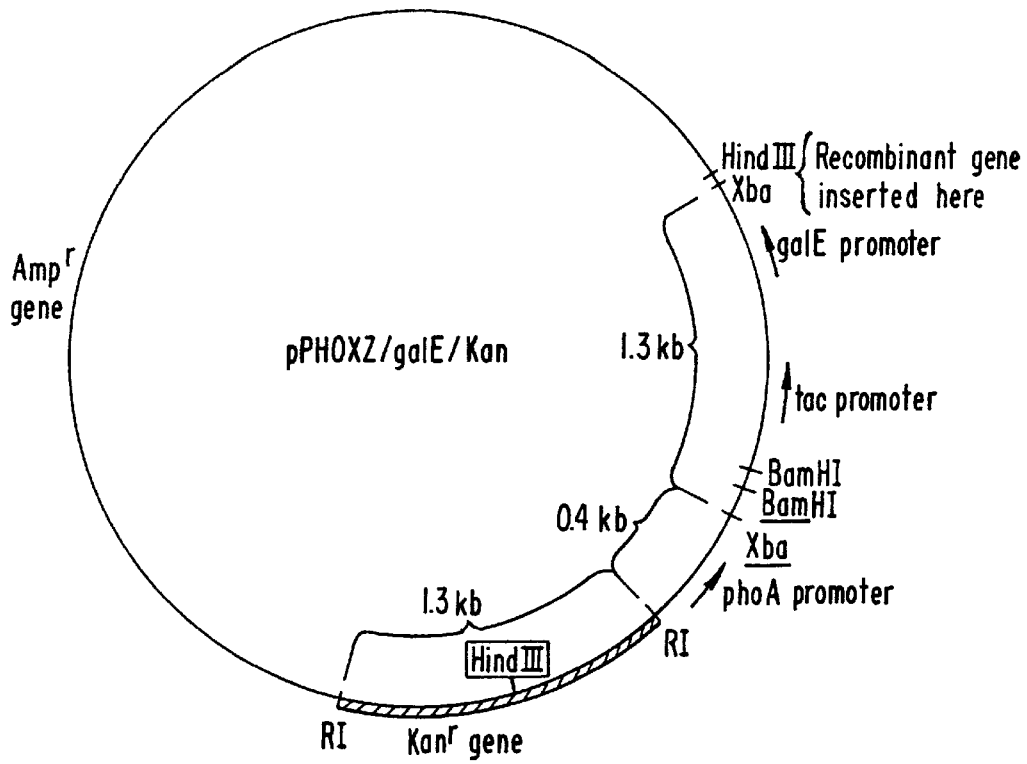
FIG. 3 is a map of the plasmid pPHOX2/galE/Kan.

The 1.3 kb Kan$^r$ gene from plasmid pUC4K (Vieira and Messing, *Gene* 19:259 (1982)) was digested EcoRI and inserted into the unique EcoRI site of the pPHOX2/galE plasmid. Colonies were selected by kanamycin resistance. The resulting plasmid is called pPHOX2/galE/Kan (FIG. 3).

Vector Improvements for Ease of Cloning

Multiple restriction sites for XbaI and HindIII in the pHOX2/galE/Kan plasmid made cloning cumbersome since the recombinant gene is inserted using these two sites. Therefore, the XbaI site at the 5' end of the galE promoter fragment and a HindIII site in the Kan$^r$ gene were removed. To delete the XbaI site, the pPHOX2/galE plasmid was partially digested with XbaI and the linearized plasmid was isolated. The cut XbaI site was filled in with Klenow polymerase to make a blunt fragment and religated. Colonies were screened by restriction mapping to identify those having a plasmid that lacked the 5' XbaI site (plasmid pPHOX2/galE$_\Delta$Xba).

Figure 4:
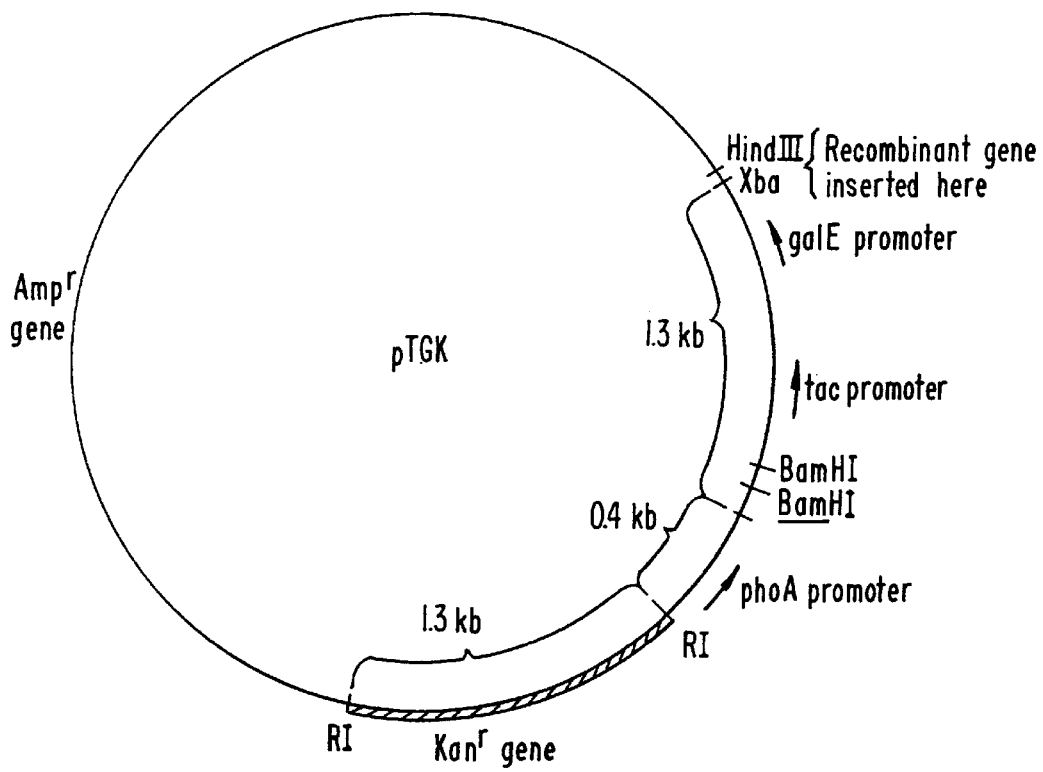
FIG. 4 is a map of the plasmid pTGK. This plasmid is essentially the same as pPHOX2/galE/Kan, except that the 5'XbaI site of the promoter region and the HindIII site in the kanamycin resistance gene (kan$^r$) have been deleted.

An oligonucleotide (ATGCATAAACTTTTGCCATTCTCAC; $_\Delta$H3 (SEQ ID NO:7)) was designed to change the AAG codon of HindIII (AAGCTT) to delete the restriction site but keep the same amino acid codon (lysine, AAA). The first PCR reaction amplified DNA from plasmid pUC4K using the $_\Delta$H3 oligonucleotide and the M13 forward primer (New England Biolabs), generating a 620 bp fragment. A second PCR reaction amplified DNA from pUC4K using the M13 reverse primer (New England Biolabs) and the fragment from the first PCR, generating a 1.3 kb fragment. The second fragment was further amplified by PCR with the forward and reverse primers. This fragment was digested with EcoRI (and HindIII to cut nonrecombinants) and ligated to an isolated linear fragment of a partial EcoRI digest of plasmid pPHOX2/galE$_A$Xba. A NheI/HindIII digest was used to determine the correct insertion site of the EcoRI fragment. This vector, which is called pTGK (FIG. 4), was deposited with the American Type Culture Collection (10801 University Boulevard, Manassas, Va. 20110–2209) on May 22, 1996 and has been assigned Accession No. 98059.

Modifications of the pTGK Vector

A number of modifications can be made to the pTGK vector. For example one can modify the vector to facilitate cloning and expression of blunt PCR fragments. To do this, pTGK is digested with XbaI and the ends are filled in with Klenow polymerase. A CCCGGG oligonucleotide is ligated to the blunt ends, recircularizing the plasmid, after which it is digested with XbaI to remove non-recombinants. Digestion with SrfI or SmaI, which make a blunt-ended cut between the CCC and GGG, results in blunt ends to which one can ligate a blunt-ended fragment obtained by PCR or other methods. By using as primers for PCR oligonucleotides that begin with the ATG of the initiation codon, the optimal spacing between the initiation codon and the ribosome binding site can be maintained (FIG. 5). This vector is called pTGKS.

Example 2

Analysis of Expression from Dual tac-gal Promoter

This experiment tested the ability of galactose to induce expression of the *S. thermophilus* UDP-gal-4-epimerase gene (galE) in *E. coli* using pHP1, which contains the gene's natural promoter as well as the tac promoter. *E. coli* strain JM101 containing pHP1 was grown overnight in LB or M9 medium which was supplemented as indicated below. All cultures were incubated overnight at 37° C. with agitation and attained a cell density equivalent to an A$_{600}$ of approximately 2–3. Cells were harvested upon reaching stationary phase and disrupted by French pressure cell treatment. UDP-galactose-4-epimerase activity was assayed as described in Kalckar et al., *Proc. Nat'l. Acad. Sci. USA* 45: 1776 (1959). A unit is defined as a $\mu$mole of substrate utilized per minute.

The results of this experiment, which are presented in Table 1, demonstrated that galactose induces expression of the epimerase gene in *E. coli*.

TABLE 1

| Growth medium | U/L, Epimerase |
|---|---|
| LB | 850 |
| LB, 10 mM Galactose | 2000 |
| M9, 0.5% Fructose, 1 mM Galactose | 2200 |
| M9, 0.5% Fructose, 10 mM Galactose | 3120 |
| M9, 1% Fructose, 10 mM Galactose | 3340 |
| M9, 1.2% Glycerol, 10 mM Galactose | 2860 |

To determine whether expression of genes other than the native galE gene is inducible by galactose when under the control of the dual promoter, we inserted a gene encoding GlcNAc transferase into pTGK. This vector was transformed into *E. coli* JM101, which was grown in M9 medium containing either fructose, fructose and galactose, or glucose as a carbon source. As shown in Table 2, expression levels were fairly low for GlcNAcT; the resulting high experimental error rendered the data inconclusive as to galactose inducibility.

TABLE 2

| pTGK/GlcNAcT | U/L, GlcNAc T |
|---|---|
| M9, Fructose | 15 |
| M9, Fructose + Galactose | 16 |
| M9, Glucose | 12 |

The tac Promoter has a Significant Effect on Expression Levels

To determine whether the tac promoter contributes to expression of genes under the control of the dual tac-gal promoter, we deleted the tac promoter from constructs expressing GlcNAc transferase or Gal transferase (Gotschlich, E.C., *J. Exp. Med.* 180: 2181–2190 (1994)). The galE promoter was present in all constructs. Strains were grown in M9+fructose+galactose and assayed for GlcNAc or Gal transferase activity. Results, shown in Table 3, demonstrate that the tac promoter contributes significantly to expression levels.

TABLE 3

| | U/L |
|---|---|
| A. GlcNAcT constructs | |
| pTGK (P$_{tac}$, P$_{galE}$, Kan) | 16 |
| pGK (P$_{galE}$, Kan) | 0.5 |
| B. GalT constructs | |
| pTGK (P$_{tac}$, P$_{galE}$, Kan) | 7 |
| pGK (P$_{galE}$, Kan) | 3 |

Effect of galE and tac Promoters on Pyruvate Kinase Expression Levels

Because the relatively low expression levels in Table 2 above prevented a statistically meaningful conclusion as to galactose inducibility of expression of a heterologous gene under the control of the dual promoter, a more highly expressed enzyme (pyruvate kinase) was chosen for the following experiments. The galE promoter was deleted from a pTGK plasmid that contained a pyruvate kinase construct, leaving the plasmid with only the tac promoter. As a control, we used the same construct but with both promoters. The ribosome binding site and spacing was identical in both constructs. The results of these experiments, shown in Table 4, demonstrate that the presence of the galE promoter region has a significant effect on expression of pyruvate kinase. Interestingly, galactose induction was observed for both constructs, including that which lacked the galE promoter.

TABLE 4

| | U/L, Pyr. kinase | |
|---|---|---|
| | P$_{tac}$ | P$_{tac,galE}$ |
| M9, 0.5% Fructose | 1202 | 3167 |
| M9, 0.5% Fructose + 10 mM Galactose | 1902 | 4377 |
| M9, 0.5% Glucose | 1208 | 2625 |

In another experiment, the tac promoter was deleted from the pyruvate kinase construct. This construct was transformed into *E. coli* and compared to strains containing either both promoters or the tac promoter only. The results of this experiment, which are presented in Table 5, demonstrate that the combined contribution of the tac and galE promoters is greater than the sum of their individual activities. Addition of galactose increases expression levels.

TABLE 5

|  | U/L, Pyr. kinase | | |
| --- | --- | --- | --- |
|  | $P_{galE}$ | $P_{tac}$ | $P_{tac,galE}$ |
| M9, 0.5% Fructose | 403 | 1420 | 3181 |
| M9, 0.5% Fructose + 10 mM Galactose | 429 | 1839 | 3635 |

Example 3

Expression of Recombinant Genes

The *E. coli* expression vector pTGK has been used to produce numerous recombinant proteins, including CMP-sialic acid synthetase from *E. coli*, UDP-glucose pyrophosphorylase from *Bacillus subtilis*, adenylate kinase from *E. coli*, pyruvate kinase from *Bacillus stearothermophilus*, sialic acid aldolase from *E. coli*, UDP-GlcNAc pyrophosphorylase from *E. coli*, rabbit muscle myokinase, Neisseria β1,4-galactosyltransferase, and Neisseria N-acetyl glucosaminyltransferase. High yields have been obtained for all of these proteins. For example, 10,000,000 U rabbit muscle myokinase were produced per kg of cells, and 3,500,000 U of pyruvate kinase per kg of cells were expressed from pTGK.

Example 4

Bacterial Fermentation Protocol using pTGK

Preparation of medium

1. Weigh out the following ingredients in a 2 liter beaker:
   - 60 g Na₂HPO₄ — Sigma S0876
   - 30 g KH₂PO₄ — Sigma P5379
   - 5 g NaCl — J. T. Baker 3628-05
   - 50 g (NH₄)₂SO₄ — J. T. Baker 0792R
2. Add 1 liter distilled water and mix to dissolve.
3. Weigh out the following ingredients in a 2 liter beaker:
   - 120 g NZAmine A — Quest Intl.
   - 50 g Yeast extract — Difco
   - 2 ml Mazu — PPG Chemical DF 204
4. Add 1 liter distilled water and mix to dissolve.
5. Add solutions from steps 2 and 4 to fermentor (e.g., New Brunswick BioFlow IV). Make to 10 liters with distilled water.
6. Autoclave fermentor for 60 min. using steam-in-place sterilization. Sterilize ports for 15 min.
7. Weigh out fructose for 50% solution:
   - 400 g Fructose — Sigma F0127
8. Make to 800 ml with distilled water and mix. Transfer to a 1 liter bottle.
9. Weigh out galactose for 20% solution:
   - 100 g Galactose — Sigma G0625
10. Make to 500 ml with distilled water and mix. Transfer to 1 liter bottle.
11. Weigh out MgSO₄ for 0.5M solution:
    - 6g MgSO₄ — Sigma M7506
12. Make to 100 ml with distilled water and mix. Transfer to 200 ml bottle.
13. Weigh out CaCl₂ for 1M solution:
    - 11 g CaCl₂ — J. T. Baker 1311-01
14. Make to 100 ml with distilled water and mix. Transfer to 200 ml bottle.
15. Autoclave the following for 45 min:
    - 50% fructose (step 8)
    - 20% galactose (step 10)
    - 0.5M MgCl₂ (step 12)
    - 1M CaCl₂ (step 14)
    - 1 liter bottle equipped with tubing for Feed pump #1
16. Weigh out kanamycin for 25 mg/ml solution:
    - 0.5 g Kanamycin — Sigma K4000

Bacterial Fermentation Protocol using pTGK (continued)

17. Make to 20 ml with distilled water and mix. Filter sterilize through 0.2 micron sterile filter.
18. Weigh out FeSO₄ immediately before inoculating culture in fermentor:
    - 1.0 g FeSO₄ — Sigma F7002
19. Make to 10 ml with distilled water and mix. Filter sterilize through 0.2 micron sterile filter.
20. Hook up 50% NH₄OH solution to Feed pump #2.

Fermentor parameters for a New Brunswick BioFlow IV Fermentor

1. Calibrate the dissolved oxygen (D.O.) probe, if necessary. Starting D.O. should be 100%.
2. Set D.O. to proportional integral derivative (P.I.D.) with a set value of 20%.
3. Set agitation to P.I.D. with a set value of 300 rpm. Change P.I.D. to D.O. setting and set at 800 rpm. The 800 value will revert back to 300 in a few seconds. This instructs the agitation to start at 300 rpm but will increase the rpm up to 800 in order to keep D.O. at 20%.
4. Set pH to P.I.D. with a set value of 6.8.
5. Set Feed #2 to base setting (feed pump #2 controls the NH₄OH addition).
6. Set temperature to P.I.D. with a set value of 37 C.
7. Set air within range of 4.3 to 4.7 liters per min.

Inoculation of fermentor

Prepare the feed bottle:
1. Add 600 ml of fructose solution and 300 ml of galactose solution to the autoclaved feed bottle. Hook up bottle to Feed #1 on fermentor.
2. Determine the absorbance at 600 nm of the grown inoculum. Dilute culture 1/10 in water in a 0.5 ml glass cuvette. Blank with water.
3. Add the following ingredients to a sterile 1 liter flask:
   - 50 ml Fructose
   - 100 ml MgSO₄
   - 1 ml CaCl₂
   - 20 ml Kanamycin
   - 2.5 ml FeSO₄
   - Add to the fermentor when cooled.
4. Add inoculum to fermentor.

Expression of Desired Protein

To obtain a protein of interest using the claimed dual promoters using a fermentor, cells are grown initially in medium containing a small amount of fructose as the carbon source. Once the cells are proliferating, usually about 5–6 hours after inoculation, a solution of galactose and fructose is fed into the medium in fed-batch mode. The feed rate can be increased during the fermentation (in a stepped or ramped fashion) as the culture becomes dense with cell growth. The carbon source feed continues through to the end of the fermentation. If desired, the polypeptide of interest is then purified from the medium (in the case of a secreted protein) or from the harvested cells.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A recombinant nucleic acid construct comprising a dual bacterial promoter operably linked to a heterologous nucleic acid that encodes a desired polypeptide, wherein the dual bacterial promoter comprises a tac promoter component and a gal promoter component.

2. The recombinant nucleic acid of claim 1, wherein the tac promoter component is a trc promoter.

3. The recombinant nucleic acid of claim 1, wherein the gal promoter component is a bacterial UDPgalactose-4-epimerase promoter.

4. The recombinant nucleic acid construct of claim 3, wherein the gal promoter component is from *Streptococcus thermophilus*.

5. The recombinant nucleic acid construct of claim 1, wherein the dual promoter results in a higher level of expression of the desired polypeptide than either the tac promoter component or the gal promoter component individually.

6. The recombinant nucleic acid construct of claim 1, wherein the heterologous nucleic acid encodes a bacterial polypeptide.

7. The recombinant nucleic acid construct of claim 6, wherein the heterologous nucleic acid is obtained from a los locus of *Neisseria gonorrhoeae*.

8. The recombinant nucleic acid construct of claim 1, wherein the heterologous nucleic acid encodes a mammalian polypeptide.

9. The recombinant nucleic acid construct of claim 1, wherein the heterologous nucleic acid encodes a fungal polypeptide.

10. The recombinant nucleic acid construct of claim 1, wherein the heterologous nucleic acid encodes a plant polypeptide.

11. The recombinant nucleic acid construct of claim 1, wherein the heterologous nucleic acid encodes CMP-sialic acid synthetase.

12. The recombinant nucleic acid construct of claim 1, wherein the heterologous nucleic acid encodes a UDP-glucose pyrophosphorylase.

13. The recombinant nucleic acid construct of claim 1, wherein the heterologous nucleic acid encodes adenylate kinase.

14. The recombinant nucleic acid construct of claim 1, wherein the heterologous nucleic acid encodes pyruvate kinase.

15. The recombinant nucleic acid construct of claim 1, wherein the heterologous nucleic acid encodes sialic acid aldolase.

16. The recombinant nucleic acid construct of claim 1, wherein the heterologous nucleic acid encodes rabbit muscle myokinase.

17. An expression vector which comprises a selectable marker and a recombinant nucleic acid construct comprising a dual bacterial promoter operably linked to a heterologous nucleic acid that encodes a desired polypeptide, wherein the dual bacterial promoter comprises a tac promoter component and a gal promoter component.

18. The expression vector of claim 17, wherein the selectable marker is a kanamycin resistance gene.

19. The expression vector of claim 17, which further comprises an origin of replication sequence which functions in *E. coli*.

20. A plasmid which is identical to a plasmid deposited with the American Type Culture Collection under Accession No. 98059.

21. A recombinant nucleic acid construct comprising a *Streptococcus thermophilus* UDPglucose-4-epimerase promoter operably linked to a heterologous nucleic acid that encodes a desired polypeptide.

22. A bacterial cell comprising a recombinant expression cassette comprising a dual bacterial promoter operably linked to a heterologous nucleic acid that encodes a desired polypeptide, wherein the dual bacterial promoter comprises a tac promoter component and a gal promoter component.

23. The bacterial cell of claim 22, wherein the gal promoter component is from *Streptococcus thermophilus*.

24. The bacterial cell of claim 22, which is *E. coli*.

25. The bacterial cell of claim 22, wherein the recombinant expression cassette is located on an independently replicating plasmid.

26. The recombinant nucleic acid construct of claim 25, wherein the heterologous nucleic acid encodes UDP-GlcNAc pyrophosphorylase.

27. The bacterial cell of claim 25, wherein the plasmid further comprises a kanamycin resistance gene.

28. The bacterial cell of claim 22, wherein the heterologous nucleic acid encodes CMP-sialic acid synthetase.

29. The bacterial cell of claim 22, wherein the heterologous nucleic acid encodes UDP-glucose pyrophosphorylase.

30. The bacterial cell of claim 22, wherein the heterologous nucleic acid encodes adenylate kinase.

31. The bacterial cell of claim 22, wherein the heterologous nucleic acid encodes pyruvate kinase.

32. The bacterial cell of claim 22, wherein the heterologous nucleic acid encodes sialic acid aldolase.

33. The bacterial cell of claim 22, wherein the heterologous nucleic acid encodes UDP-GlcNAc pyrophosphorylase.

34. The bacterial cell of claim 22, wherein the heterologous nucleic acid encodes rabbit muscle myokinase.

35. The bacterial cell of claim 22, wherein the heterologous nucleic acid is obtained from a los locus of *Neisseria gonorrhoeae*.

36. A method of making a desired polypeptide, the method comprising culturing in an appropriate medium bacterial cells comprising a recombinant expression cassette comprising a dual bacterial promoter operably linked to a heterologous nucleic acid that encodes a desired polypeptide under conditions that allow expression of the desired polypeptide, wherein the dual bacterial promoter comprises a tac promoter component and a gal promoter component.

37. The method of claim 36, wherein the gal promoter component is from *Streptococcus thermophilus*.

38. The method of claim 36, wherein the bacterial cells are *E. coli*.

39. The method of claim 36, wherein the bacterial cells are cultured in a medium comprising kanamycin.

40. The method of claim 36, wherein expression of the desired polypeptide is induced by the presence of galactose in the medium.

41. The method of claim 36, wherein the heterologous nucleic acid encodes UDP-glucose pyrophosphorylase.

42. The method of claim 36, wherein the heterologous nucleic acid encodes adenylate kinase.

43. The method of claim 36, wherein the heterologous nucleic acid encodes pyruvate kinase.

44. The method of claim 36, wherein the heterologous nucleic acid encodes sialic acid aldolase.

45. The method of claim 36, wherein the heterologous nucleic acid encodes UDP-GlcNAc pyrophosphorylase.

46. The method of claim 36, wherein the heterologous nucleic acid encodes rabbit muscle myokinase.

47. The method of claim 36, wherein the heterologous nucleic acid encodes CMP-sialic acid synthetase.

48. The method of claim 36, wherein the heterologous nucleic acid is obtained from a los locus of *Neisseria gonorrhoeae*.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 1561 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: promoter
      (B) LOCATION: 362..389
      (D) OTHER INFORMATION: /note= "tac promoter"

(ix) FEATURE:
      (A) NAME/KEY: promoter
      (B) LOCATION: 1438..1467
      (D) OTHER INFORMATION: /note= "galE promoter"

(xi) SEQUENCE DESCRIPTION: SEQ ID NO:1:

```
GTAAAGAAGT TATGGAGCNT CTTNGTCAGT AAAAAGTTAT TTTTTTCAAC AGCGTTCATA      60

AAGTGTCACG GCCGGAGAAT TATAGTCGCT TGGTTTTTAT TTTTTAAGTA TTGGTAACTA     120

GTACGCAAGT TCACGTAAAA AGGGTAACTA GATAGACGAN GGTCCGGNGT AGAGGATCCG     180

GGCTTATCGA CTGCACGGTG CACCAATGCT TCTGGGTCAG GCAGCCATCG GAAGCTGTGG     240

TATGGCTGTG CAGGTCGTAA ATCACTGCAT AATTCGTGTC GCTCAAGGCG CACTCCCGTT     300

CTGGATAATG TTTTTTGCGC CGACATCATA ACGGTTCTGG CAAATATTCT GAAATGAGCT     360

GTTGACAATT AATCATCGGC TCGTATAATG TGTGGAATTG TGAGCGGATA ACAATTTCAC     420

ACAGGAAACA GAATTCCCGG GGATCCGTCG ACCTGCAGCT AAAAATGCGG TAGCTTCTGA     480

TTATCCAAAA TGCCAACTTT GTATGGAAAA TGAAGGTTAT TTGGGTCGCA TTAATCACCC     540

AGCCCGCAGC AATCACCGTG TTGTTCGTTT CCAAATGGAA GACAAGGAGT GGGGCTTCCA     600

ATACTCGCCT TATGCCTACT TTAACGAACA TTCTATCTTC TTTTATGGTA AGCACGAACC     660

AATGCACATC AGTCCATTGA CGTTTGGCCG TCTCCTAACA ATTGTTGAAG CATTCCCCTG     720

GTTACTTCGC AGGTTCAAAT GCCGATCTTC CAATTGTAGG TGGTTCAATT CTTACACATG     780

AACACTATCA AGGTGGTCGC CATACCTTCC CAATGGAAGT AGCAGGCATT AAAGAAAAAG     840

TTAGCTTTGA TGGTTACTCT GATGTTGAGG CTGGCATCGT TAATTGGCCT ATGTCTGTTC     900

TTCGTCTAAG AAGTGAAGAC AAGGGAAGAC TTATCGCTCT TGCAACTAAA ATCCTAAATT     960

GCTGGCGTGG TTATTCAGAC GAAAAAGCTG GGGTCTTGGC TGAGTCTGAT GGACAACCTC    1020

ACCACACCAT TACTCCAATT GCTCGTAGAA AAGACGGCAA ATTTGAATTG GATTTGGTTC    1080

TTCGTGACAA TCAAACTTCT GAAGAATATC CAGACGGTAT CTATCACCCA CATAAAGATG    1140

TTCAACATAT TAAGAAAGAA AATATTGGTT TGATTGAAGT TATGGGATTG GCCATTCTTC    1200

CACCTCGTTT GAAAACAGAA CTTAAAGATG TTGAAGATTA TCTATTAGGT CAAGGTAACC    1260

AAGTTGCTCC AATTCACCAA GAATGGGCAG ATGAACTCAA AGCTCAAATC CGAATATTAC    1320

GGCTGAGGAA GTGACAGAAG TTGTTCGACA ATCTGTTGCA GATATCTTTG CTCGTGTACT    1380

AGAAGATGCA GGTGTTTATA AGACTAATAG TGAAGGCTTG GATCAGTTTA AAGCATTTGT    1440

AGATTTTGTA AATTTAGCTG ATTAATTGTT TTTTCTGAAG AAAGGAGGTC TAGAGTCGAC    1500
```

```
CTGCAGGCAT GCAAGCTTCT GTTTTGGCGG ATGAGAGAAG ATTTTCAGCC TGATACAGAT      1560

T                                                                      1561

(2) INFORMATION FOR SEQ ID NO:2:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

GAAAAGAAGT CTAGANNNAT GNNNNNN                                            27

(2) INFORMATION FOR SEQ ID NO:3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

GAAAAGAAGT CTAGCCCGGG CTAGA                                              25

(2) INFORMATION FOR SEQ ID NO:4:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

GAAAAGAAGT CTAGCCCATG NNNNNNN                                            27

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

GCTCTAGACG ATCCGTCCGG CGTA                                               24

(2) INFORMATION FOR SEQ ID NO:6:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

ATTCTAGACC TCCTTTCTCA GAAAAAACAA TT                                      32
```

-continued (2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

ATGCATAAAC TTTTGCCATT CTCAC                                      25